United States Patent [19]

Okabe et al.

[11] 3,983,230

[45] Sept. 28, 1976

[54] ANTIBIOTIC SIOMYCIN A DERIVATIVES AND PRODUCTION THEREOF

[75] Inventors: Kei Okabe, Yao; Mikao Mayama, Ikeda; Shinzo Matsuura, Itami, all of Japan

[73] Assignee: Shionogi & Co., Ltd., Japan

[22] Filed: Mar. 7, 1975

[21] Appl. No.: 556,411

Related U.S. Application Data

[63] Continuation-in-part of Ser. No. 461,432, April 15, 1974, abandoned.

[30] Foreign Application Priority Data

Apr. 18, 1973 Japan.................................. 48-43900

[52] U.S. Cl. ................................................. 424/117
[51] Int. Cl.² ........................................ H61K 35/74

[58] Field of Search...................................... 424/117

[56] References Cited

OTHER PUBLICATIONS

Ebata et al., J. of Antibiotics, Aug. 1969, pp. 364–368.

*Primary Examiner*—Jerome D. Goldberg
*Attorney, Agent, or Firm*—Wenderoth, Lind & Ponack

[57] ABSTRACT

Antibiotic siomycin A derivatives produced by reaction of siomycin A with a dicarboxylic acid. The compounds have excellent characteristics, particularly in their solubility in comparison with that of siomycin A, and are useful as medicaments.

10 Claims, 16 Drawing Figures

ANTIBIOTIC SIOMYCIN A DERIVATIVES AND PRODUCTION THEREOF

This is a continuation-in-part of Ser. No. 461,432, filed Apr. 15, 1974, now abandoned.

This invention relates to useful antibiotic siomycin A derivatives. More particularly, it relates to water-soluble half esters of siomycin A with dicarboxylic acids and inorganic salts thereof. It further relates to a process for their production.

Siomycin is an antibiotic produced by cultivating a strain of Streptomyces sioyaensis which was originally isolated in 1959 from a sample of soil collected at Shioya, Kobe, Japan, and which has been deposited with the American Type Culture Collection under the accession number ATCC 13989. Siomycin shows a broad antibacterial spectrum, particularly against gram-positive bacteria and mycobacteria (U.S. Pat. No. 3,082,153). As it has since been found that Streptomyces sioyaensis produces two other antibiotics, the siomycin A, B and C have been isolated from cultures of Streptomyces sioyaensis (J. Antibiotics, 22, p 364–368, 1969). Characterization of siomycin A has been carried out, but its complete chemical structure has not yet been elucidated.

Siomycin A has a disadvantage in its solubility; it is soluble in dioxane and slightly soluble in methanol, ethanol, chloroform, and butanol, but because it is almost insoluble in water, its use in pharmaceutical preparations is necessarily limited. In view of its very remarkable antibacterial activities, e.g. the minimum inhibitory concentration against gram-positive bacteria is $0.1–0.78 \mu g/ml$, enhancement of its solubility in various solvents, particularly in water, is strongly desired.

As the result of various investigations to this end, new half esters of siomycin A have been discovered, produced by reaction of siomycin A with dicarboxylic acid, which are easily soluble in dilute alkali solvents without any substantial loss in their antibacterial activity. Further, it has been discovered that the half esters of siomycin A can be converted into corresponding inorganic salts which have excellent antibacterial activity and remarkably improved solubility in various solvents, particularly in water. Still further, it has been discovered that the products obtained by the present invention are useful as medicaments for treatment of various bacterial infections. The present invention has been accomplished on the basis of these discoveries, and may be clearly seen to afford significant advantages in view of the aforementioned background.

Accordingly, an object of the invention is to provide novel siomycin A derivatives. Another object of the invention is to provide the half esters of siomycin A with dicarboxylic acid. Another object of the invention is to provide half esters of siomycin A with dicarboxylic acid, having high antibacterial activity against gram-positive bacteria and mycobacteria. Another object of the invention is to provide half esters of siomycin A with dicarboxylic acid, having a highly improved solubility in various solvents. Another object of the invention is to provide inorganic salts of the half ester of siomycin A with dicarboxylic acid, showing highly enhanced solubility in various solvents and an antibacterial spectrum against gram-positive bacteria and mycobbacteria. Another object of the invention is to embody a process for preparing the half esters of siomycin A with dicarboxylic acid and inorgnaic salts thereof in high purity and good yield. These and other objects will be apparent to those conversant with the art to which the present invention pertains from the following description.

According to the present invention, the half esters of siomycin A and inorganic salts thereof can be prepared by reacting siomycin A with dicarboxylic acids described below or their reactive derivatives in an inert solvent, and, if desired, converting the resulting product into the corresponding inorganic salt in a conventional manner.

The dicarboxylic acids used in forming the half esters of siomycin A of this invention, are the aliphatic dicarboxylic acids containing 2 to 15 carbon atoms e.g. ethanedioic acid, propanedioic acid, 2-methylpropanedioic acid, 2-ethylpropanedioic acid, 2-butylpropanedioic acid, butanedioic acid, 2-methylbutanedioic acid, 2,3-dimethylbutanedioic acid, 2-ethylbutanedioic acid, 3-propylbutanedioic acid, cis-2-butenedioic acid, trans-2-butenedioic acid, 2-methyl-2-butenedioic acid, 2-ethyl-2-butenedioic acid, 2-ethyl-3-methyl-2-butenedioic acid, 2-butynedioic acid, pentanedioic acid, 2-methylpentanedioic acid, 3-methylpentanedioic acid, 2-methyl-3-ethylpentanedioic acid, 2-ethyl-3-propylpentanedioic acid, 2-pentenedioic acid, 2-methyl-2-pentenedioic acid, 2-methyl-3-pentenedioic acid, 2-ethyl-2-pentenedioic acid, 2-butyl-3-pentenedioic acid, 2-pentynedioic acid, hexanedioic acid, 2-methylhexanedioic acid, 2-ethylhexanedioic acid, 2-pentylhexanedioic acid, 2,4-dimethylhexanedioic acid, 2-methyl-5-methylhexanedioic acid, 2-hexenedioic acid, 3-methyl-2-hexenedioic acid, 2,4-hexadienedioic acid, 2-methyl-2,4-hexadienedioic acid, 3-ethyl-2,4-hexadienedioic acid, 3-hexynedioic acid, heptanedioic acid, 2-methylheptanedioic acid, 3-methylheptanedioic acid, 4-propylheptanedioic acid, 2,3-dimethylheptanedioic acid, 2-heptenedioic acid, 5-methyl-2-heptenedioic acid, 2,4-heptadienedioic acid, octanedioic acid, 2-methyloctanedioic acid, 2,3-dimethyloctanedioic acid, 2,3,4-trimethyloctanedioic acid, 2-methyl-3-ethyloctanedioic acid, 2-octenedioic acid, 2,4-octadienedioic acid, 2,4,6-octatrienedioic acid, nonanedioic acid, 2-methylnonanedioic acid, 2,5-dimethylnonanedioic acid, decanedioic acid, 3-methyldecanedioic acid, undecanedioic acid, 5-methylundecanedioic acid, dodecanedioic acid, tridecanedioic acid, tetradecanedioic acid, pentadecanedioic acid; cycloalkane dicarboxylic acid e.g. cyclopropane dicarboxylic acid, cyclobutane-1,2-dicarboxylic acid, 4-methylcyclobutane-1,2-dicarboxylic acid, cyclopentane-1,2-dicarboxylic acid, 4-ethylcyclopentane-1,2-dicarboxylic acid, cyclohexane-1,2-dicarboxylic acid, 3-methylcyclohexane-1,2-dicarboxylic acid, 4-methylcyclohexane-1,3-dicarboxylic acid, cycloheptane-1,2-dicarboxylic acid; and monocyclic aryl dicarboxylic acid e.g. 1,2-benzenedicarboxylic acid, 3-methyl-1,2-benzenedicarboxylic acid, 3-ethyl-4-methyl-1,2-benzenedicarboxylic acid, 4-propyl-1,2-benzenedicarboxylic acid, 1,3-benzenedicarboxylic acid, 2-methyl-1,3-benzenedicarboxylic acid, 4,5-dimethyl-1,3-benzenedicarboxylic acid, 4-methyl-5-ethyl-1,3-benzenedicarboxylic acid, 1,4-benzenedicarboxylic acid, 2-methyl-1,4-benzenedicarboxylic acid, 2-methyl-5-propyl-1,4-benzenedicarboxylic acid.

Though the said dicarboxylic acids in their free form may be used as acylating agents in forming the half esters of siomycin A of this invention, they may preferably be used in their active derivative forms, e.g. acid anhydrides, acid halides, active amide derivatives, active ester derivatives, ketene derivatives, acid azido derivatives and other reagents having an equivalent effect. Particularly, the acid anhydrides of the dicarboxylic acid may be favorably used. These active derivatives of the dicarboxylic acid may be prepared from the corresponding dicarboxylic acid according to conventional methods.

The preparation of the half esters of siomycin A of the invention can be effected by use of at least one mole of dicarboxylic acid per mole of siomycin A.

The reaction may be carried out at temperatures from 0° to 150°C for about 30 minutes to 10 hours and, if necessary, in the presence of a catalyst conventionally used in acylation. For example, when using the dicarboxylic acid in its free form as the acylating agent, it is preferable that the reaction is conducted in the presence of an acid-catalyst, e.g., hydrochloric acid, sulfuric acid, nitric acid, phosphoric acid, carbonic acid, boron fluoride and the like. When carboxylic anhydrides and acyl halides of the dicarboxylic acid are used as the acylating agent, it is preferred that the reaction is carried out in the presence of a base-catalyst selected from inorganic bases such as ammonium hydroxide, alkali metal hydroxides (e.g., potassium hydroxide and sodium hydroxide) and alkaline earth metal hydroxides, and organic bases such as lower alkyl amines and heterocyclic amines (e.g. pyridine).

The inert solvent to be employed in the present invention may be, for example, chloroform, trichloroethane, dioxane, dimethylformamide, dimethylsulfoxide, pyridine or a mixture thereof capable of dissolving both starting materials and not undesirably affecting the reaction.

The starting material, namely siomycin A, can be prepared by cultivating a strain of Streptomyces sioyaensis in an aqueous nutrient medium under aerobic conditions at a temperature of from about 25° to 32°C for a period of from 72 to 120 hours and recovering the accumulated antibiotic from the fermentation broth, as described previously (cf. U.S. Pat. No. 3,082,153, J. Antibiotics 22 P 364–368, 1969). Alternatively, a crude substance containing siomycin A may also be used starting material for the present process.

The half esters of siomycin A with dicarboxylic acid are made up of carbon, oxygen, hydrogen, nitrogen and sulfur. The half esters of siomycin A have structure in which one or more of about 5 hydroxy groups of siomycin A is esterified with one of two carboxyl groups of dicarboxylic acid. The compounds are hereinafter referred to as half esters -I, -II and -III of siomycin A with the dicarboxylic acid.

It may be assumed that the differences between half esters -I, -II and -III of siomycin A with the dicarboxylic acid reside in the number and position of the ester group in the siomycin A moiety, and the number of the ester group in the half ester -I of siomycin A with the dicarboxylic acid is more greater than that in the half esters -II and -III of siomycin A with the dicarboxylic acid.

The proportions in which the half esters -I, -II and -III of siomycin A with the dicarboxylic acid are produced depend upon the reaction conditions. If the reaction is carried out for a prolonged time at an elevated temperature and a greater than molar amount of the dicarboxylic acid is used, there can be afforded the half esters -I of siomycin A with the dicarboxylic acid as a main product. It is generally preferred that the reaction conditions are be varied in accordance with the acylating agent employed as raw material to give mainly the intended half ester compound, because the proprotions in which the half esters -I, -II and -III of siomycin A with the dicarboxylic acid produced differ according to the acylating agent employed even under the same reaction conditions.

The isolation and purification of the half esters of siomycin A can be effected with good yield in a conventional manner.

The thus produced half esters of siomycin A can be easily converted into the corresponding salts, e.g., lithium salt, sodium salt, potassium salt, calcium salt, ammonium salt and the like, in a conventional manner.

The half esters of siomycin A and salts thereof are very stable powdery substances. They are useful as medicaments and veterinary drugs because they have higher solubility and better antibacterial activity in vivo than siomycin A itself. Further, the products contained in the present invention are very stable and retain their antibacterial activities for a long time, whilst their acute toxicites are very low.

The various excellent characteristics of the compounds of the invention will be shown hereinafter together with the experimental data.

The half esters of siomycin A and inorganic salts thereof are easily soluble in various solvents, permitting various pharmaceutical preparations. The half esters of siomycin A are very easily soluble in dilute alkaline solution because they have in most cases at least one free carboxyl group. Their sodium salts are also very soluble in water, and dilute alkaline solution, although siomycin A is almost insoluble in these solvents.

The solubility in various solvents of several specific products obtained by the process of the present invention are shown in Table 1 in comparison with the solubility of siomycin A.

TABLE 1

Solubility in 0.1% aqueous solution of sodium hydrogencarbonate of siomycin A and its derivatives (solubility in distilled water in the case of sodium salts of siomycin A derivatives)

| Compound | Solubility (%) |
| --- | --- |
| Siomycin A | 0.00015 |
| Half ester -I of siomycin A with butanedioic acid | 2.0 |
| Sodium salt of half ester -I of siomycin A with butanedioic acid | 20.0 |
| Half ester -II of siomycin A with butanedioic acid | 1.0 |
| Sodium salt of half ester -II of siomycin A with butanedioic acid | 3.0 |
| Half ester -I of siomycin A with pentanedioic acid | 2.5 |
| Sodium salt of half ester -I of siomycin A with pentenedioic acid | 10.0 |
| Half ester -II of siomycin A with pentanedioic acid | 1.0 |
| Sodium salt of half ester -II of siomycin A with pentanedioic acid | 3.0 |
| Half ester -I of siomycin A with hexanedioic acid | 1.0 |
| Sodium salt of half ester -I of siomycin A with hexanedioic acid | 5.0 |
| Half ester -II of siomycin A with hexanedioic acid | 0.5 |
| Sodium salt of half ester -II of siomycin A with hexanedioic acid | 3.0 |
| Half ester -III of siomycin A with hexanedioic acid | 0.5 |
| Sodium salt of half ester -III of siomycin A with hexanedioic acid | 3.0 |
| Half ester -I of siomycin A with heptanedioic acid | 1.0 |
| Sodium salt of half ester -I of | |

-continued

| Compound | Solubility (%) |
|---|---|
| siomycin A with heptanedioic acid | 5.0 |
| Half ester -II of siomycin A with heptanedioic acid | 0.5 |
| Sodium salt of half ester -II of siomycin A with heptanedioic acid | 3.0 |
| Half ester -III of siomycin A with heptanedioic acid | 0.5 |
| Sodium salt of half ester -III of siomycin A with heptanedioic acid | 3.0 |
| Half ester -I of siomycin A with cis-butenedioic acid | 1.0 |
| Sodium salt of half ester -I of siomycin A with cis-butenedioic acid | 4.0 |
| Half ester -II of siomycin A with cis-butenedioic acid | 1.0 |
| Sodium salt of half ester -II of siomycin A with cis-butenedioic acid | 4.0 |
| Half ester -I of siomycin A with cis-2-methylbutenedioic acid | 0.5 |
| Sodium salt of half ester -I of siomycin A with cis-2-methylbutenedioic acid | 4.0 |
| Half ester -II of siomycin A with cis-2-methylbutenedioic acid | 0.5 |
| Sodium salt of half ester -II of siomycin A with cis-2-methylbutenedioic acid | 2.5 |
| Half ester -III of siomycin A with cis-2-methylbutenedioic acid | 1.0 |
| Sodium salt of half ester -III of siomycin A with cis-2-methylbutenedioic acid | 5.0 |
| Half ester -I of siomycin A with cyclohexane-1,2-dicarboxylic acid | 0.5 |
| Sodium salt of half ester -I of siomycin A with cyclohexane-1,2-dicarboxylic acid | 4.0 |
| Half ester -II of siomycin A with cyclohexane-1,2-dicarboxylic acid | 0.5 |
| Sodium salt of half ester -II of siomycin A with cyclohexane-1,2-dicarboxylic acid | 2.0 |

It is apparent from Table 1 that the half esters of siomycin A of the present invention, and the sodium salts thereof, are far more soluble in both 0.1% aqueous solution of sodium hydrogencarbonate and distilled water than siomycin A.

The half esters of siomycin A and salts thereof show activities against a variety of microorganisms. Table 2 shows the antibacterial spectra of the half esters of siomycin A and the sodium salts thereof, compared with that of siomycin A.

TABLE 2

Antibacterial spectra of siomycin A and its derivatives

| Compound | Test organism Minimum inhibitory concentration mcg/ml | | | | | |
|---|---|---|---|---|---|---|
| | A | B | C | D | E | F |
| Siomycin A | 0.39 | 0.78 | 0.39 | 0.39 | 0.1 | 0.1 |
| Half ester -II of siomycin A with butanedioic acid | 6.25 | 12.5 | 6.25 | 6.25 | 1.56 | 1.56 |
| Sodium salt of half ester -II of siomycin A with butanedioic acid | 6.25 | 25 | 6.25 | 6.25 | 1.56 | 3.13 |
| Sodium salt of half ester -II of siomycin A with pentanedioic acid | 3.13 | 6.25 | 1.56 | 1.56 | 0.39 | 0.39 |
| Sodium salt of half ester -II of siomycin A with hexanedioic acid | 0.78 | 1.56 | 1.56 | 0.78 | 0.10 | 0.20 |
| Sodium salt of half ester -II of siomycin A with heptanedioic acid | 3.13 | 6.25 | 3.13 | 3.13 | 0.2 | 0.78 |
| Sodium salt of half ester -III of siomycin A with heptanedioic acid | 0.78 | 1.56 | 1.56 | 0.78 | 0.1 | |
| Sodium salt of half ester -II of siomycin A with octanedioic acid | 1.56 | 1.56 | 3.13 | 1.56 | 0.1 | 0.2 |
| Sodium salt of half ester -III of siomycin A with octanedioic acid | 0.39 | 0.78 | 1.56 | 0.78 | <0.025 | 0.05 |
| Sodium salt of half ester -I of siomycin A with dodecanedioic acid | >50 | >50 | >50 | >50 | 12.5 | 25 |
| Sodium salt of half ester -II of siomycin A with cis-butenedioic acid | 6.25 | 12.5 | 3.13 | 3.13 | 0.78 | 1.56 |
| Sodium salt of half ester -II of siomycin A with cis-methylbutenedioic acid | 1.56 | 12.5 | 3.13 | 3.13 | 0.39 | 0.78 |
| Sodium salt of half ester -III of siomycin A with cis-methylbutenedioic acid | 1.56 | 6.25 | 3.13 | 1.56 | 0.39 | 0.78 |
| Sodium salt of half ester -II of siomycin A with cyclohexane-1,2-dicarboxylic acid | 6.25 | 12.5 | 12.5 | 6.25 | 0.78 | 1.56 |

A: *Bacillus subtilis* PCI 219
B: *Bacillus anthracis*
C: *Staphylococcus aureus* FDA 219PJC-1
D: *Staphylococcus aureus* 80257
E: *Diplococcus pneumoniae* type I
F: *Streptococcus pyogenes* C-203

Table 2 shows that the half esters of siomycin A with the dicarboxylic acid and their sodium salts are highly active against gram-positive bacteria.

The therapeutic effect of sodium salts of the half ester of siomycin A with dicarboxylic acid in mice against experimental infections are shown in Table 3.

TABLE 3

Therapeutical effect of siomycin A and its derivatives in mice.

| | ED$_{50}$ (mg/kg) | |
|---|---|---|
| | A | B |
| Siomycin A | 23.2 | 75.2 |
| Sodium salt of half ester -II of siomycin A with butanedioic acid | 16.5 | |
| Sodium salt of half ester -II of siomycin A with pentanedioic acid | 4.4 | 3.5 |
| Sodium salt of half ester -II of siomycin A with hexanedioic acid | 2.5 | 2.1 |
| Sodium salt of half ester -III of siomycin A with heptanedioic acid | 2.5 | 3.1 |

A: *Diplococcus pneumoniae* type I
B: *Streptococcus pyogenes* C-203

A group of 10 mice weighing 19–21 g were infected with a standardized inoculum of *Diplococcus pneumoniae* type or *Streptococcus pyogenes* C-203 by intraperitoneal injection.

The sodium salts of half esters of siomycin A with the dicarboxylic acid were administered subcutaneously to the mice at 0, 4 and 8 hours after infection and survival of infected mice was examined for 7 days after infection.

It is apparent from Table 3 that the sodium salts of the half esters of siomycin A with the dicarboxylic acid have a much better therapeutic effect than siomycin A.

Acute toxicities of the half ester of siomycin A with the dicarboxylic acid were studied in mice weighing 19 to 21 g. The intraperitoneal LD$_{50}$ values in a group of 5 mice are shown in Table 4.

TABLE 4

Acute toxicity of siomycin A derivatives

| Compound | LD$_{50}$ for mice (mg/Kg) |
|---|---|
| Half ester -II of siomycin A with pentanedioic acid | 250–500 |
| Half ester -II of siomycin A with hexanedioic acid | 250–500 |
| Half ester -III of siomycin A with heptanedioic acid | 250–500 |

From Table 4, it is apparent that the half esters of siomycin A with the dicarboxylic acid have low acute toxicities.

It should be noted that the test data given herein are shown only as examples. Since the other compounds of the present invention have almost the same characteristics and advantages as medicaments as those for which test data are given, the products of the present invention are highly useful and have advantages for therapeutic purpose such as the treatment of various bacterial infections in human beings and domestic animals.

The siomycin A derivatives of the present invention can be administered orally or locally in pharmaceutically conventional forms, e.g. injections, liquids, suspensions, emulsions, ointments or tablets with suitable carriers, stabilizers, emulsifiers, preservatives and/or wetting agents, where a therapeutically effective amount of the active ingredient is contained. For example, the siomycin A derivatives can be administered orally, subcutaneously, or intravenously to humans and domestic animal at a dosage of 0.1 mg to 100 mg per Kg body weight.

The following examples are given solely for the purpose of illustration and are not to be construed as limitation of this invention, many variations of which are possible.

EXAMPLE 1

Siomycin A (10.0 g) is dissolved in pyridine (60 ml) and butanedioic acid anhydride (6.0 g) is added to the mixture. The resultant mixture is kept with stirring at 93° to 95°C for an hour in oil bath. Distilled water (60 ml) and chloroform (100 ml) are added to the reaction mixture, and then the resultant solution is vigorously shaken. The chloroform phase is evaporated under reduced pressure to remove the solvent, then benzene is added to the resulting residue. The benzene-insoluble part is dissolved in a mixture of chloroform and methanol (8 : 2 by volume). The resulting mixture is chromatographed on a column of silica gel (particle size 0.05–0.2 mm, made by Merk company) and eluted with a mixture of chloroform and methanol with a progressively increasing concentration of methanol. The fractions containing the half ester of siomycin A with butanedioic acid are collected and concentrated. The concentrated solution is applied to a silica gel GF plate (made by Merk company) and the plate is developed with a mixture of chloroform and methanol (8 : 2 by volume). The part containing the half ester -I of siomycin A with butanedioic acid is extracted with a mixture of chloroform and methanol and the resulting solution is concentrated. To the concentrated solution is added ethyl acetate to obtain the half ester of siomycin A with butanedioic acid (precipitate). The yield is 60%.

The half ester -II of siomycin A with butanedioic acid is similarly obtained from the fractions containing the half ester -II of siomycin A with butanedioic acid, which are separated by the said column chromatography. The yield is 15%.

° Half ester -I of siomycin A with butanedioic acid
Yellowish powder.
Melting point: 265°–280°C (decomposition)

The compound shows no definite decomposition point. It turns yellow at around 200°C then changes progressively to brown with decomposition. Rf value on thin-layer chromatography on silica gel GF (made by Merck company): Rf = 0 [chloroform - methanol (8 : 2 by volume) solvent]

Figure 1:
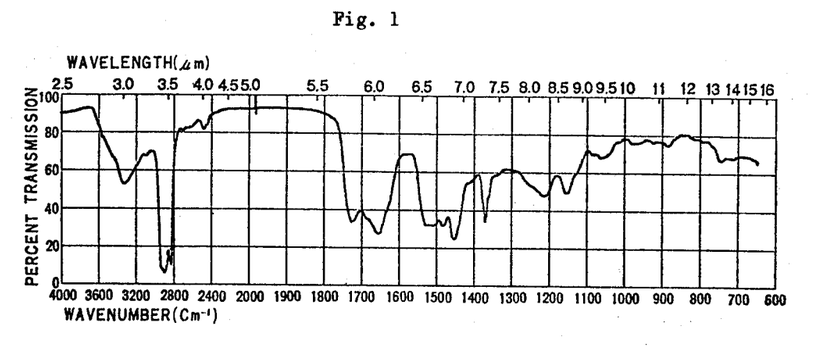
Figure 2:
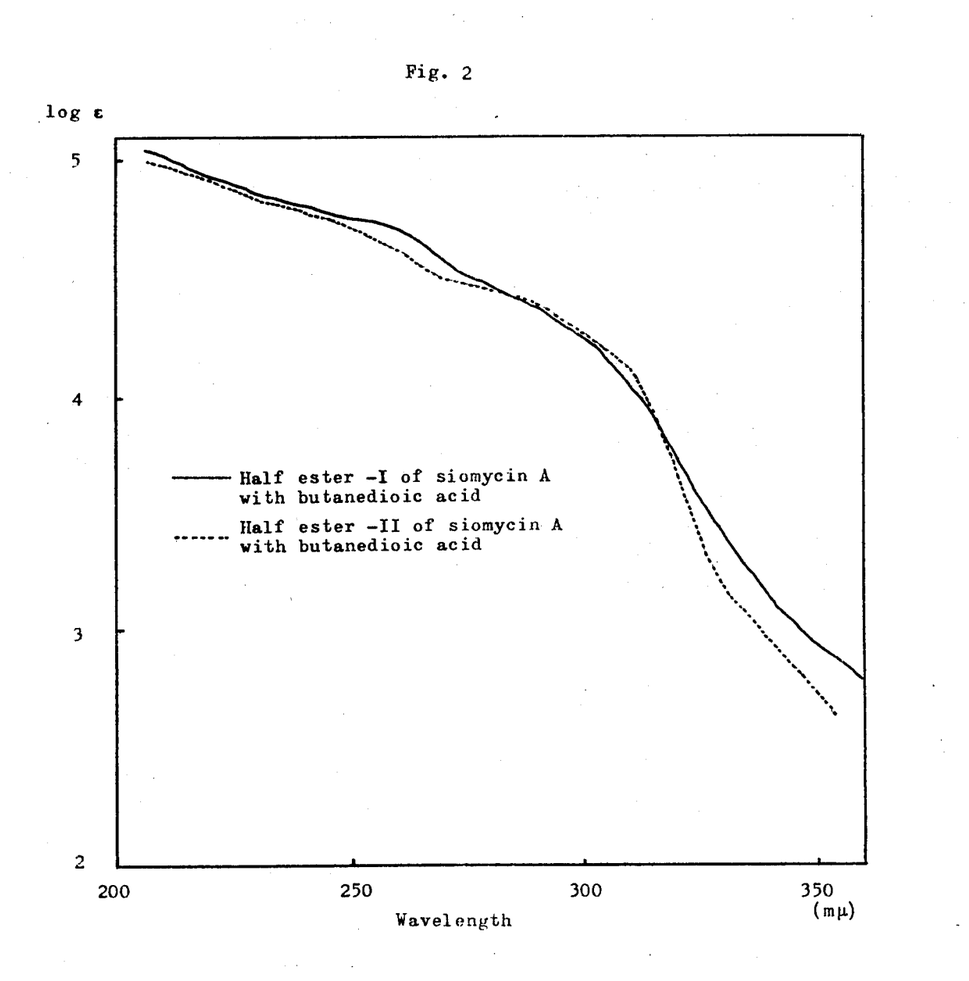

Neutralization equivalent: 500
Solubility: Well soluble in a mixture of chloroform and methanol, and in an aqueous solution of sodium hydrogen-carbonate. Almost insoluble in ethyl ether, chloroform and water. Specific optical rotation: $[\alpha]_D^{25}$ −63.2±2.0° (c=0.525, in methanol)
Infrared absorption spectrum: $\gamma_{max}^{Nujol}$ cm$^{-1}$ : 3345, 1735, 1663 (broad) (See FIG. 1)
Ultraviolet absorption spectrum $\lambda_{max}^{MeOH}$ nm (log$\epsilon$): 255 (4.75 shoulder) (See FIG. 2)
Elementary analysis: Anhydrous compound; C, 50.42 %; H, 5.10 %; N, 14.57 %; S, 7.93 %, Hydrate of the compound; C, 45.77 %; H, 5.45 %; N, 12.21 %; S, 7.62 %; H$_2$O, 10.68 %.

° Half ester -II of siomycin A with butanedioic acid
Colorless or pale yellowish powder.
Melting point: The compound shows no definite dcomposition Point. It turns yellow at around 200°C, then changee progressively to brown, then deep brown.

Rf value on thin-layer chromatography on silica gel GF (made by Merck company): Rf = 0.3 [chloroform - methanol (8 : 2 by volume) solvent]

Neutralization equivalent: 780

Solubility: Well soluble in a mixture of chloroform and methanol, and in an aqueous solution of sodium hydrogen-carbonate. Almost insoluble in ethyl ether, chloroform and water. Specific optical rotation $[\alpha]_D^{25}$ −144.0 ± 3.7° (c = 0.507, in methanol)

Figure 3:
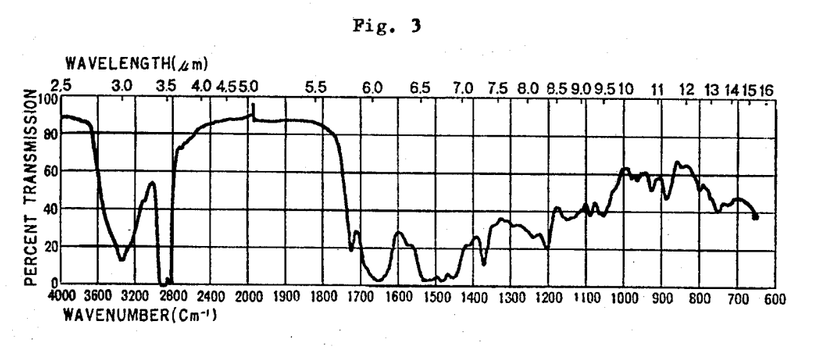

Infrared absorption spectrum: $\gamma_{max}^{Nujol}$ cm$^{-1}$ : 3360, 1732, 1660 (broad) (See FIG. 3)

Ultraviolet absorption spectrum: $\lambda_{max}^{MeOH}$ nm (log$\epsilon$): 245 (4.76 shoulder), 290 (4.40 shoulder), 310 (4.13 shoulder) (See FIG. 2)

Elementary analysis: Anhydrous compound; C, 48.52%; H, 5.04 %; N, 14.76 %; S, 8.02%; Hydrate of the compound; C, 45.69 %; H, 5.35 %; N, 13.32 %; S, 7.89 %; H$_2$O, 8.80 %.

EXAMPLE 2

The half ester -II of siomycin A with butanedioic acid (0.8 g) prepared by the manner described in Example 1 is dissolved in 0.1 % aqueous solution of sodium hydrogen-carbonate (70.8 g). The solution is filtered to remove the small amounts of impurity, then freeze-dried to obtain the sodium salt of half ester -II of siomycin A with butanedioic acid as a powder. The yield is 95 %.

EXAMPLE 3

The half esters -I and -II of siomycin A with pentanedioic acid are prepared according to the manner described in Example 1 except that pentanedioic acid anhydride is employed instead of butanedioic acid anhydride. The yields of the half esters -I and -II of siomycin A with pentanedioic acid are about 50 % and 20 %, respectively.

° Half ester -I of siomycin A with pentanedioic acid
Yellowish powder.

Melting point: The compound shows no definite melting point or decomposition point. It changes progressively from yellow to brown at around 200°C.

Rf value on thin-layer chromatography on silica gel GF (made by Merck company): Rf = 0 [chloroform - methanol (8 : 2 by volume) solvent]

Solubility: Well soluble in a mixture of chloroform and methanol, and in sodium hydrogencarbonate solution. Almost insoluble in ethyl ether, chloroform and water.

Specific optical rotation: $[\alpha]_D^{22.5}$ −68.7±2.2° (c=0.504, in methanol)

Figure 4:
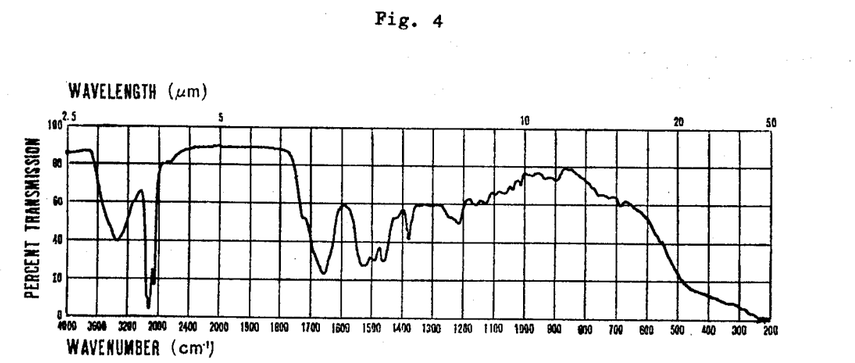

Infrared absorption spectrum: $\gamma_{max}^{Nujol}$ cm$^{-1}$ : 3340, 1725, 1658 (broad) (See FIG. 4)

Figure 5:
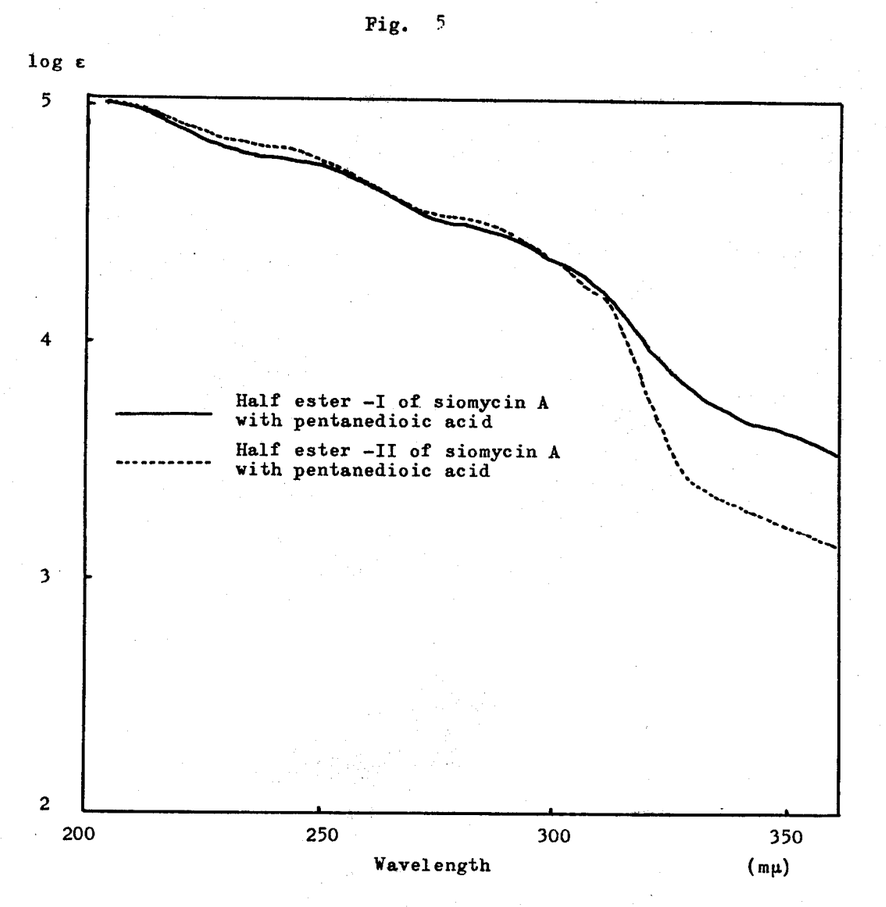

Ultraviolet absorption spectrum: $\lambda_{max}^{MeOH}$ nm (log$\epsilon$): 245 (4.78 shoulder), 285 (4.49 shoulder), (See FIG. 5)

Elementary analysis: Anhydrous compound; C, 49.61 %; H, 5.14 %; N, 14.37 %; S, 8.53 %, Hydrate of the compound; C, 46.35 %; H, 5.70 %; N, 11.51 %; S, 7.75 %; H$_2$0, 10.45 %.

° Half ester -II of siomycin A with pentanedioic acid
Pale yellowish powder.

Melting point: The compound shows no definite melting or decomposition point. It turns yellow at around 200°C, then changes progressively to brown.

Rf value on thin-layer chromatography on silica gel GF (made by Merck company): Rf = 0.49 [chloroform - methanol (8 : 2 by volume) solvent]

Solubility: Well soluble in a mixture of chloroform and methanol, and in aqueous solution of sodium hydrogencarbonate. Almost insoluble in ethyl ether, chloroform and water.

Specific optical rotation: $[\alpha]_D^{22.5}$ −84.0±4.1° (c=0.306, in methanol)

Figure 6:
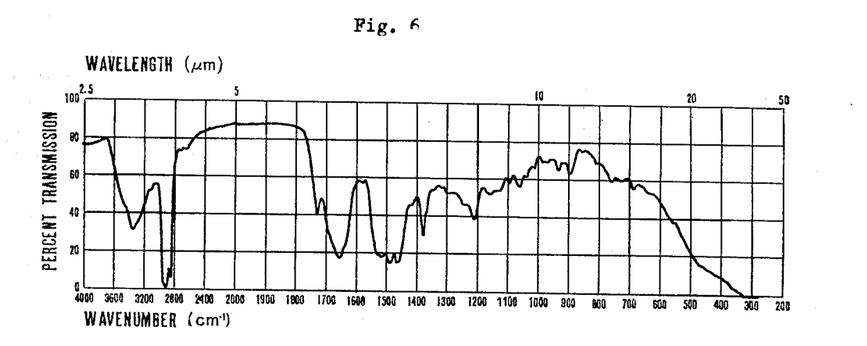

Infrared absorption spectrum: $\gamma_{max}^{Nujol}$ cm$^{-1}$ : 3340, 1730, 1655 (broad) (See FIG. 6)

Ultraviolet absorption spectrum: $\lambda_{max}^{MeOH}$ nm (log$\epsilon$): 245 (4.71 shoulder) 285 (4.51 shoulder) 310 (4.20 shoulder) (See FIG. 5)

Elementary analysis: Anhydrous compound: C, 51.59 %; H, 5.18 %; N, 15.03 %; S, 9.30 %; Hydrate of the compound: C, 49.06 %; H, 5.04 %; N, 12.85 %; S, 8.48 %; H$_2$O, 7.13 %.

EXAMPLE 4

Siomycin A (5 g) is dissolved in pyridine (30 ml), and hexanedioic acid anhydride (3.0 g) is added to the mixture. The resultant mixture is stirred at 93° to 95°C for an hour in an oil bath, then distilled water (100 ml) is added to the reaction mixture. The resulting mixture is extracted with 80 ml of chloroform then with 20 ml of chloroform. These chloroform extracts are combined and evaporated under reduced pressure to leave residue (about 10.3 g). The residue is redissolved in chloroform (100 ml) and distilled water (150 ml) is added to the solution. The mixture is shaken and filtered. The precipitate is dissolved in a mixture of chloroform and methanol (8 : 2 by volume), and the resulting solution is evaporated under reduced pressure to give the half ester -I of siomycin A with hexanedioic acid (1.50 g) as a pale yellowish powder.

The said chloroform phase is evaporated under reduced pressure to give a residue (6.1 g). The residue is dissolved in a mixture of chloroform and methanol (8 : 2 by volume). The resulting solution is applied to a silica gel GF plate to give the half ester -I of siomycin A with hexanedioic acid according to the manner described in Example 1. The yield is 54.6 %.

The fractions eluted which contain the half esters -II and -III of siomycin A with hexanedioic acid are collected and applied to a silica gel GF plate to give the half esters -II (yield 20 %) and -III (yield 10 %) of siomycin A with hexanedioic acid according to the manner described in Example 1.

° Half ester -I of siomycin A with hexanedioic acid
Pale yellowish powder.

Melting point: The compound shows no definite melting point or decomposition point. It turns yellow at around 200°C, then changes progressively to brown.

Rf value on thin-layer chromatography on silica gel GF (made by Merck company): Rf = 0.10 [chloroform-methanol (8 : 2 by volume) solvent]

Solubility: Well soluble in a mixture of chloroform and methanol, and in an aqueous solution of sodium hydrogencarbonate. Almost insoluble in ethyl ether, chloroform, methanol and water. Specific optical rotation: $[\alpha]_D^{23}$ −61.5±3.3° (c=0.314, in a mixture of chloroform and methanol (1 : 1))

Figure 7:
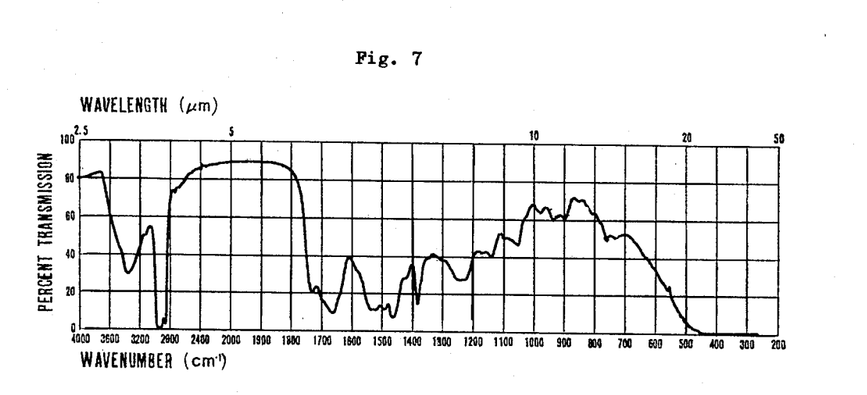

Infrared absorption spectrum: $\gamma_{max}^{Nujol}$ cm$^{-1}$ : 3350, 1726, 1660 (broad) (See FIG. 7)

Figure 8:
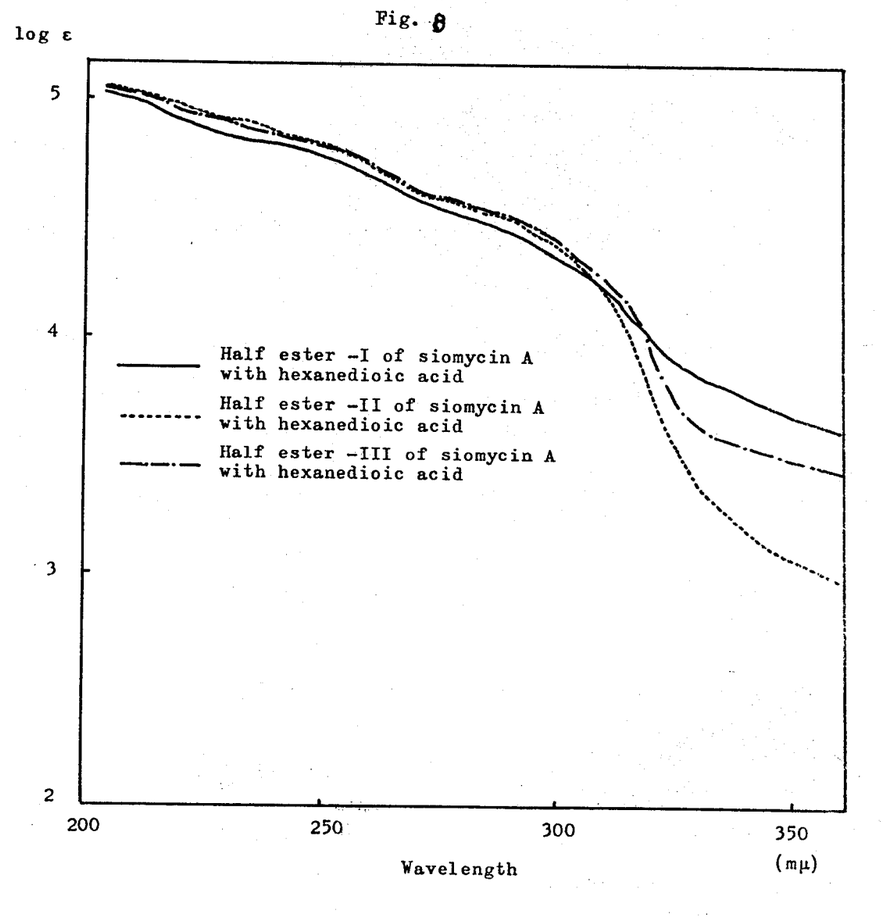

Ultraviolet absorption spectrum: $\lambda_{max}^{MeOH}$ nm (log$\epsilon$); 245 (4.79 shoulder), 290 (4.44 shoulder). (See FIG. 8)

Elementary analysis: Anhydrous compound; C, 51.42 %; H, 5.36 %; N, 13.32 %; S, 8.26 %, Hydrate of the compound; C, 49.25 %; H, 5.39 %; N, 12.29 %; S, 7.81 %; H$_2$O, 5.44 %.

○ Half ester -II of siomycin A with hexanedioic acid
Colorless crystalline powder.

Melting point: The compound shows no definite melting point or decomposition point. It turns yellow at around 200°C, then changes progressively to brown. Rf value on thin-layer chromatography on silica gel GF (made by Merck company): Rf = 0.56 [Solvent: chloroform - methanol (8 : 2 by volume)]

Solubility: Well soluble in a mixture of chloroform and methanol, and in an aqueous solution of sodium hydrogencarbonate. Almost insoluble in ethyl ether, chloroform, methanol and water. Specific optical rotation: $[\alpha]_D^{23.5}$ −118.4±5.3° (c=0.304, in a mixture of chloroform and methanol (1 : 1))

Figure 9:
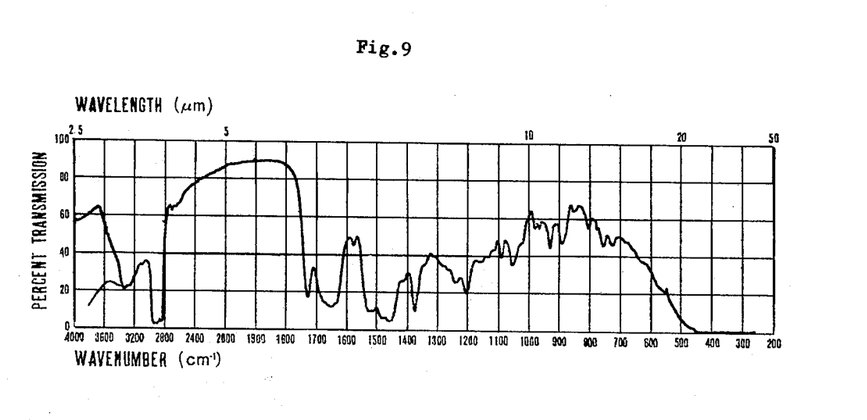

Infrared absorption spectrum: $\gamma_{max}^{Nujol}$ cm$^{-1}$ : 3340, 1731, 1653 (broad) (See FIG. 9)

Ultraviolet absorption spectrum: $\lambda_{max}^{MeOH}$ nm (logε): 245 (4.83 shoulder), 285 (4.52 shoulder), 310 (4.20 shoulder) (See FIG. 8)

Elementary analysis: Anhydrous compound; C, 51.18 %; H, 5.24 %; N, 14.73 %; S, 8.86 %, Hydrate of the compound; C, 48.74 %; H, 5.56 %; N, 13.57 %; S, 8.65 %; H$_2$O, 3.83 %.

○ Half ester -III of siomycin A with hexanedioic acid
Pale yellowish powder.

Melting point: The compound shows no definite melting point or decomposition point. It turns yellow at around 200°C then changes progressively to brown. Rf value on thin-layer chromatography on silica gel GF (made Merck company): Rf = 0.48 [Solvent: chloroform-methanol (8 : 2 by volume)]

Solubility: Well soluble in a mixture of chloroform and methanol, and in an aqueous solution of sodium hydrogencarbonate. Almost insoluble in ethyl ether, chloroform, methanol and water.

Specific optical rotation: $[\alpha]_D^{23.5}$ −140.2±6.0° (c=0.301, in a mixture of chloroform and methanol (1 : 1 by volume))

Figure 10:
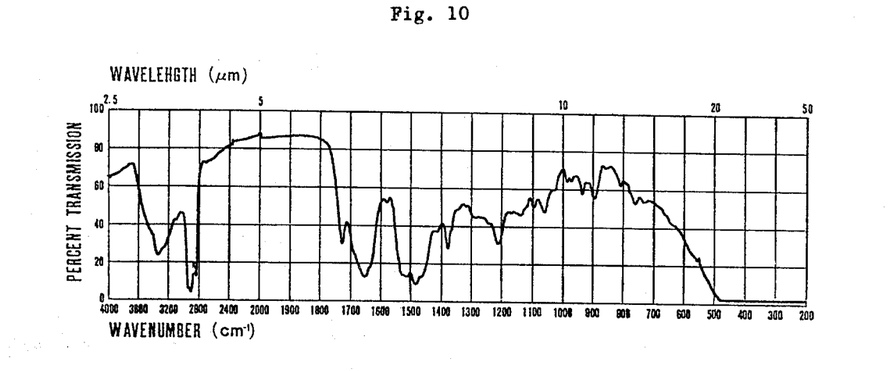

Infrared absorption spectrum: $\gamma_{max}^{Nujol}$ cm$^{-1}$ : 3360, 1728, 1653 (broad) (See FIG. 10)

Ultraviolet absorption spectrum: $\lambda_{max}^{MeOH}$ nm (logε): 245 (4.83 shoulder), 285, (4.53 shoulder), 310 (4.25 shoulder) (See FIG. 8)

Elementary analysis: Anhydrous compound; C, 51.89 %; H, 5.77 %; N, 14.56 %; S, 8.97 %, Hydrate of the compound; C, 49.37 %; H, 5.53 %; N, 13.78 %; S, 8.46 %; H$_2$O, 5.44 %.

EXAMPLE 5

The half ester -II or siomycin A with hexanedioic acid (38 mg) is dissolved in a 0.1 % aqueous solution of sodium hydrogencarbonate (3.36 g) with stirring at room temperature. After being allowed to stand for 3 hours, the reaction mixture is filtered to remove impurity, and the resulting filtrate (pH 6.2) is freeze-dried to give the sodium salt of the half ester -II of siomycin A with hexanedioic acid as colorless powder. The yield is 98 %.

○ Sodium salt of the half ester -II of siomycin A with hexanedioic acid.
White powder.

Melting point: The compound becomes yellow at around 200°C, then changes progressively to brown. Rf value on thin-layer chromatography on silica gel GF (made by Merck company): Rf = 0.56 [Solvent: chloroform-methanol (8 : 2 by volume)]

Figure 11:
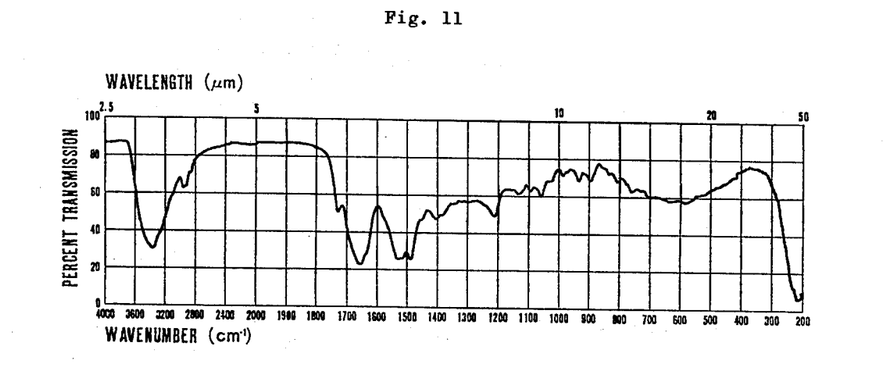
Figure 12:
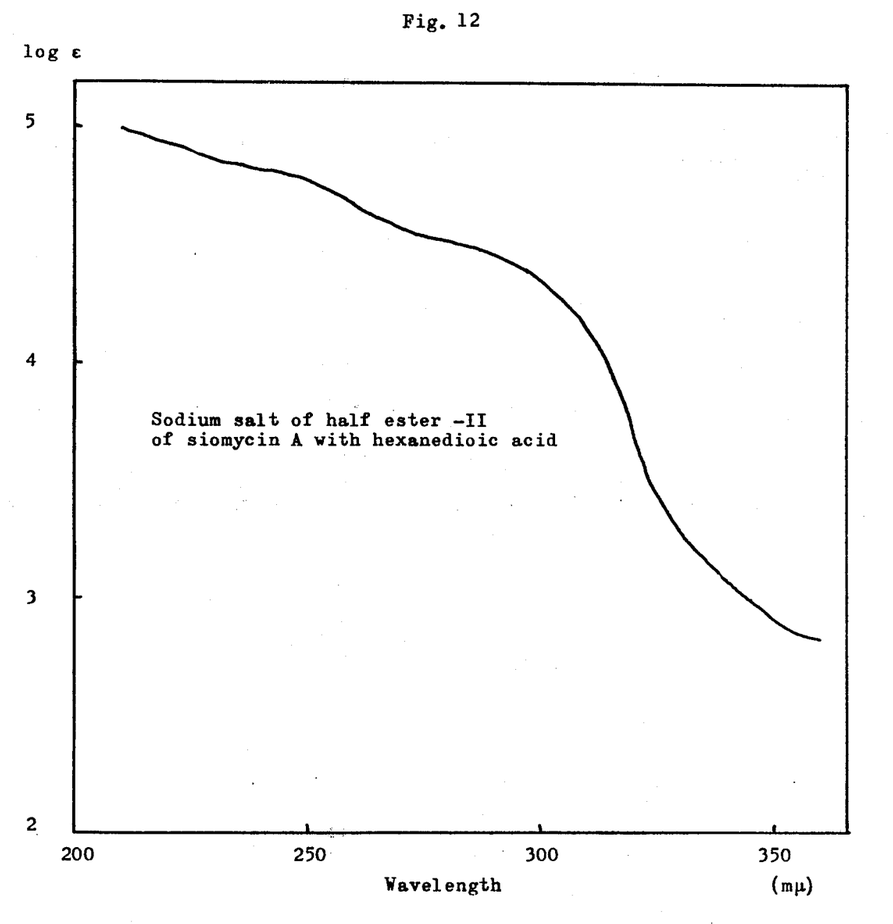

Solubility: Well soluble in a mixture of chloroform and methanol, methanol and water. Almost insoluble in ethyl ether and chloroform. Specific optical rotation: $[\alpha]_D^{23}$ −70.2±8.2° (c=0.134, H$_2$O). Infrared absorption spectrum: $\gamma_{max}^{Nujol}$ cm$^{-1}$ : 3380, 1728, 1655 (See FIG. 11) Ultraviolet absorption spectrum: $\lambda_{max}^{MeOH}$ nm (logε): 245 (4.80 shoulder), 285 (4.49 shoulder), 310 (4.15 shoulder) (See FIG. 12)

Elementary analysis: Hydrate of the compound; C, 47.34 %; H, 5.44 %; N, 12.96 %; S, 7.99 %; Na, 2.48 %; H$_2$O, 7.77 %.

EXAMPLE 6

To a solution of siomycin A (10.0 g) in pyridine (6 ml) is added heptanedioic acid anyhydride (0.6 g), and the resultant mixture is stirred at 100°C in oil bath for an hour. Distilled water (10 ml) and chloroform (20 ml) are then added and the mixture is shaken. The chloroform layer is evaporated under reduced pressure to remove the solvent. The residue obtained (1.6 g) is redissolved in chloroform (50 ml), distilled water is added, and the mixture shaken. The chloroform layer is washed with water and evaporated under reduced pressure to remove the solvent. The resulting residue is subjected to column and thin-layer chromatographies to give the half ester -I (yield 60 %), -II (yield 20 %) and -III (yield 15 %) of siomycin A with heptanedioic acid according to the manner described in Example 1.

○ Half ester -I of siomycin A with heptanedioic acid
Pale yellowish powder.

Melting point: The compound shows no definite melting or decomposition point. It turns yellow at around 200°C, then changes progressively to brown. Rf value on thin-layer chromatography on silica gel GF (made by Merck company): Rf = 0.10 [Solvent; chloroform-methanol (8 : 2 by volume)]

Solubility: Well soluble in a mixture of chloroform and methanol, and in an aqueous solution of sodium hydrogencarbonate. Almost insoluble in ethyl ether, chloroform, methanol and water.

Figure 13:
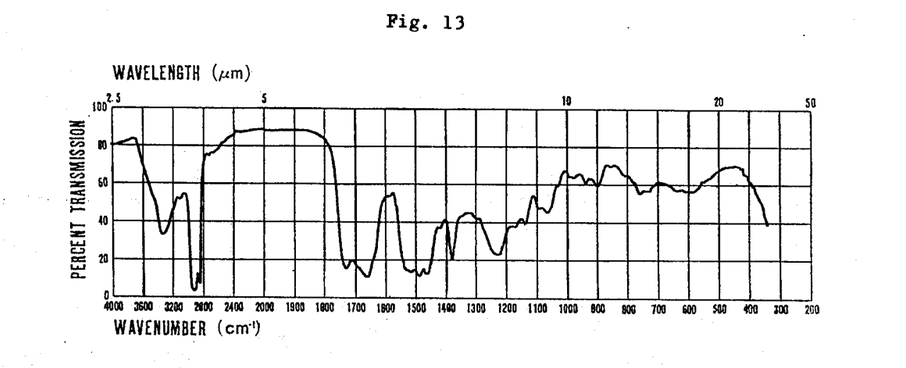
Figure 14:
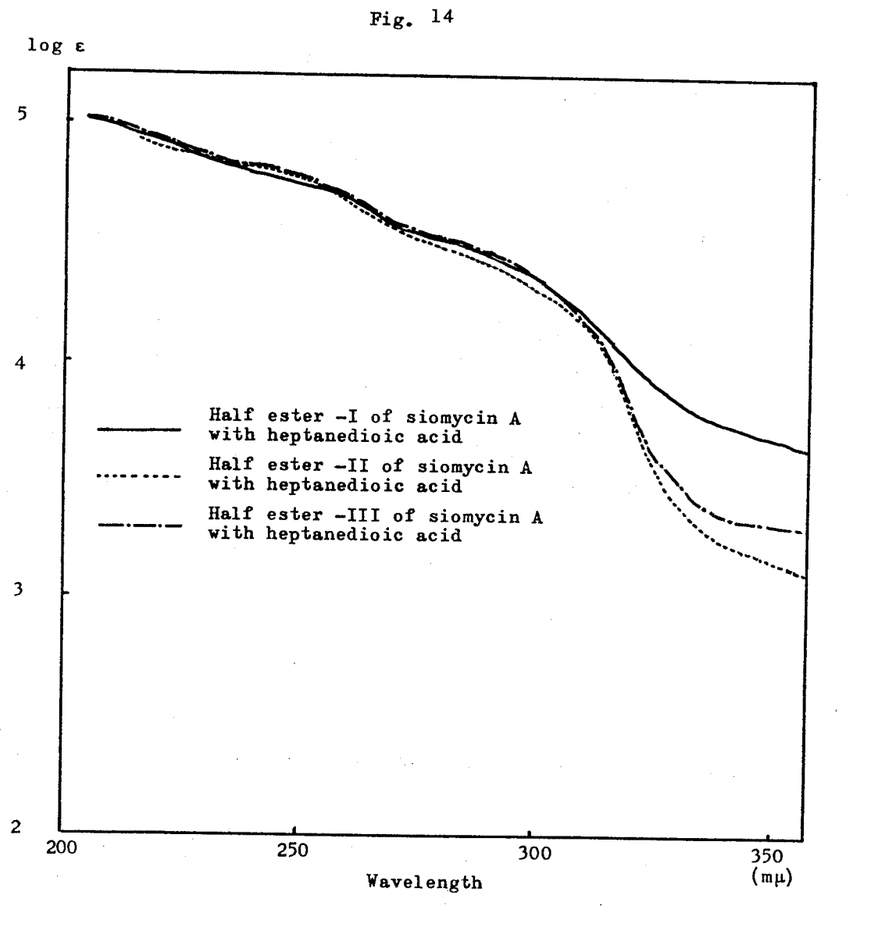

Specific optical rotation: $[\alpha]_D^{23.5}$ −73.2±3.5° (c=0.325, in a mixture of chloroform and methanol (1 : 1 by volume)) Infrared absorption spectrum: $\gamma_{max}^{Nujol}$ cm$^{-1}$ : 3340, 1728, 1657 (broad) (See FIG. 13) Ultraviolet absorption spectrum: $\lambda_{max}^{MeOH}$ nm (logε): 250 (4.76 shoulder), 290 (4.45 shoulder) (See FIG. 14)

Elementary analysis: Anhydrous compound; C, 52.41 %; H, 5.62 %; N, 13.41 %; S, 8.26 %; Hydrate of the compound; C, 50.21 %; H, 5.60 %; N, 12.54 %; S, 7.91 %; H$_2$O, 3.56 %.

○ Half ester -II of siomycin A with heptanedioic acid
Pale yellowish powder.

Melting point: The compound shows no definite melting or decomposition point. It turns yellow at around 200°C, then changes progressively to brown. Rf value on thin-layer chromatography on silica gel GF (made by Merck company):

Rf = 0.47 [Solvent: chloroform-methanol (8 : 2 by volume)]

Solubility: Well soluble in a mixture sodium chloroform and methanol and in an aqueous solution of sodim hydrogencarbonate.

Almost insoluble in ethyl ether, chloroform, methanol and water.

Specific optical rotation: $[\alpha]_D^{23.5}$ −128.6±5.5° (c=0.308, in a mixture of chloroform and methanol (1 : 1 by volume))

Figure 15:
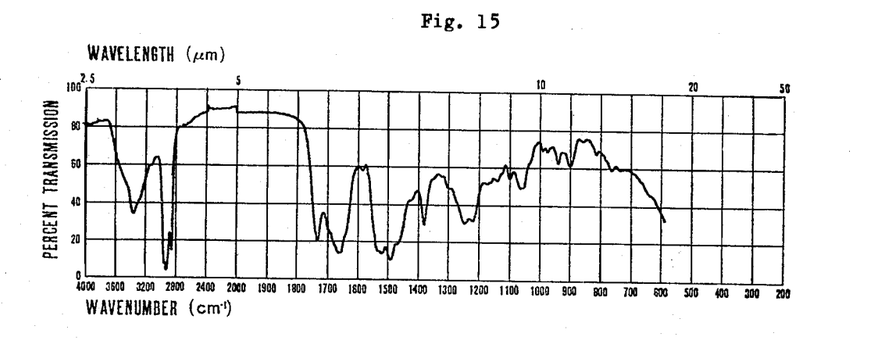

Infrared absorption spectrum: $\gamma_{max}^{Nujol}$ cm$^{-1}$ : 3363, 1730, 1656 (broad) (See FIG. 15)

Ultraviolet absorption spectrum: $\lambda_{max}^{MeOH}$ nm (logε): 245 (4.78 shoulder), 290 (4.43 shoulder), 310 (4.14 shoulder) (See FIG. 14)

Elementary analysis: Anhydrous compound; C, 53.21 %; H, 5.72 %; N, 14.07 %; S, 8.73 %, Hydrate of the compound; C, 50.68 %; H, 5.63 %; N, 13.48 %; S, 8.36 %; $H_2O$, 4.94 %.

° Half ester -III of siomycin A with heptanedioic acid

Almost colorless crystalline powder.

Melting point: The compound shows no definite melting or decomposition point. It turns yellow at around 200°C then changes progressively to brown. Rf value on thin-layer chromatography on silica gel GF (made by Merck company):

Rf = 0.56 [Solvent: chloroform-methanol (8 : 2 by volume)]

Solubility: Well soluble in a mixture of chloroform and methanol, and in an aqueous solution of sodium hydrogencarbonate.

Almost insoluble in ethyl ether, chloroform, methanol and water.

Specific optical rotation: $[\alpha]_D^{23.5}$ −119.3±5.0° (c=0.322, in a mixture of chloroform and methanol (1 : 1 by volume))

Figure 16:
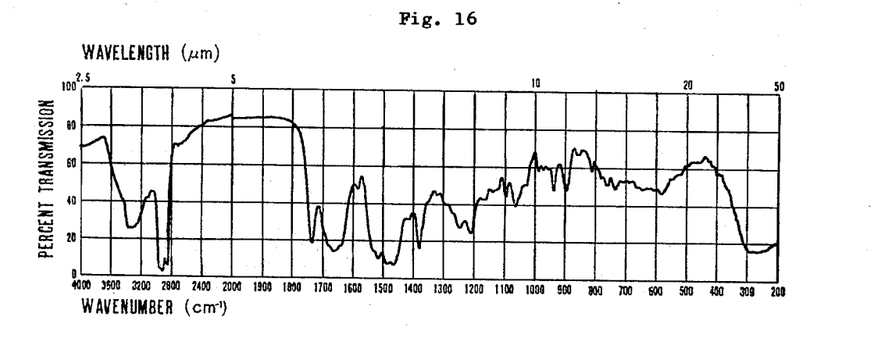

Infrared absorption spectrum: $\gamma_{max}^{Nujol}$ cm$^{-1}$: 3330-3380, 1731, 1663 (broad) (See FIG. 16)

Ultraviolet absorption spectrum: $\gamma_{max}^{MeOH}$ nm (logλ): 250 (4.78 shoulder), 290 (4.47 shoulder), 310 (4.19 shoulder) (See FIG. 14)

Elementary analysis: Anhydrous compound; C, 52.00 %; H, 5.34 %; N, 14.33 %; S, 8.73 %, Hydrate of the compound; C, 48.74 %; H, 5.49 %; N, 13.36 %; S, 8.38 %; $H_2O$, 6.40 %.

EXAMPLE 7

To a solution of siomycin A (300 mg) in pyridine (1.8 ml) is added octanedioic acid anhydride (1.80 mg), and the resultant mixture is stirred at 100°C in an oil bath for an hour. Distilled water (5 ml) and chloroform (10 ml) are added and the mixture shaken. The chloroform layer is then evaporated under reduced pressure to remove the solvent. According to the manner described in Example 1, the obtained residue (483 mg) is subjected to a column and thin-layer chromatographies to give the half esters -I (yield 30 %, -II (yield 20 %) and -III (yield 15 %), of siomycin A with octanedioic acid.

° Half ester -I of siomycin A with octanedioic acid

Powder. Rf value on thin-layer chromatography on silica gel GF (made by Merck company); Rf = 0.10–0.30 [Solvent: chloroform-methanol (8 : 2 by volume)]

Solubility: Well soluble in a mixture of chloroform and methanol, and in an aqueous solution of sodium hydrogencarbonate. Almost insoluble in ethyl ether, chloroform, methanol and water.

Infrared absorption spectrum: $\gamma_{max}^{Nujol}$ cm$^{-1}$ : 1730, 1670

Elementary analysis: Anhydrous compound; C, 52.37 %; H, 5.78 %; N, 13.34 %; S, 8.29 %, Hydrate of the compound; C, 50.34 %; H, 5.42 %; N, 12.73 %; S, 8.11 %; $H_2O$, 4.20 %.

° Half ester -II of siomycin A with octanedioic acid

Powder. Rf value on thin-layer chromatography on silica gel GF (made by Merck company) : Rf = 0.53 [Solvent: chloroform-methanol (8 : 2 by volume)]

Solubility: Well soluble in a mixture of chloroform and methanol, and in an aqueous solution of sodium hydrogencarbonate. Almost insoluble in ethyl ether, chloroform, methanol and water.

Infrared absorption spectrum: $\gamma_{max}^{Nujol}$ cm$^{-1}$ : 1730, 1660

Elementary analysis: Anhydrous compound; C, 52.88 %; H, 5.76 %; N, 14.27 %; S, 8.72 %, Hydrate of the compound; C, 50.48 %; H, 5.46 %; N, 13.19 %; S, 8.30 %; $H_2O$, 5.21 %.

° Half ester -III of siomycin A with octadedioic acid

Powder. Rf value on thin-layer chromatography on silica gel GF (made by Merck company); Rf = 0.49 [Solvent: chloroform-methanol (8 : 2 by volume)]

Solubility: Well soluble in a mixture of cloroform and methanol, and in an aqueous solution of sodium hydrogencarbonate. Almost insoluble in ethyl ether, chloroform, methanol and water.

Infrared absorption spectrum: $\gamma_{max}^{Nujol}$ cm$^{-1}$: 1730, 1660–1670

Elementary analysis: Anhydrous compound; C, 52.31 %; H, 5.35 %; N, 14.23 %; S, 8.68 %, Hydrate of the compound; C, 49.63 %; H, 5.72 %; N, 13.36 %; S, 8.37 %; $H_2O$, 6.23 %.

EXAMPLE 8

To a solution of siomycin A (0.3 g) in pyridine (1.8 ml) is added dodecanedioic acid anhydride (0.18 g), and the resultant mixture is stirred at 97°C in an oil bath for an hour. A small amount of cold distilled water and chloroform (10 ml) are then added and the mixture shaken. The resulting chloroform layer is evaporated under reduced pressure to remove the solvent. According to the manner described in Example 1, the oily residue obtained (0.34 g) is subjected to column and thin-layer chromatographies to give the half esters -I (yield 20 %) and -II (yield 30 %) of siomycin A with dodecanedioic acid.

° Half ester -I of siomycin A with dodecanedioic acid

Powder.

Melting point: The compound turns brown at about 200°C and decomposes at over 250°C. Rf value on thin-layer chromatography on silica gel GF (made by Merck company): Rf = 0–0.35 [Solvent: chloroform-methanol (8 : 2 by volume)]

Solubility: Well soluble in a mixture of chloroform and methanol, and in an aqueous solution of sodium hydrogencarbonate. Almost insoluble in ethyl ether, chloroform, methanol and water.

Infrared absorption spectrum: $\gamma_{max}^{Nujol}$ cm$^{-1}$: 1730, 1660–1670

Elementary analysis: Anhydrous compound; C, 52.49 %; H, 5.69 %; N, 13.27 %; S, 8.24 %, Hydrate of the compound; C, 50.37 %; H, 5.76 %; N, 12.68 %; S, 7.95 %; $H_2O$, 4.76 %.

° Half ester -II of siomycin A with dodecanedioic acid

Powder.

Melting Point: The compound turns brown at about 200°C and decomposes at over 250°C. Rf value on thin-layer chromatography on silica gel GF (made by Merck company) Rf = 0.58 [Solvent: chloroform-methanol (8 : 2 by volume)]

Solubility: Well soluble in a mixture of chloroform and methanol, and in an aqueous solution of sodium hydrogencarbonate. Almost insoluble in ethyl ether, chloroform, methanol, and water. Infrared absorption spectrum: $\gamma_{max}^{Nujol}$ cm$^{-1}$: 1735, 1660–1670

Elementary analysis: Anhydrous compound; C, 52.97 %; H, 5.78 %; N, 14.13 %; S 8.49 %, Hydrate of the compound; C, 50.70 %; H, 5.68 %; N, 13.41 %; S, 8.31 %; $H_2O$, 5.12 %.

EXAMPLE 9

To a solution of siomycin A (10.0 g) in pyridine (6 ml) is added cis-butenedioic acid anhydride (0.7 g) and the mixture is treated as described in Example 1 to give the half ester -I (yield 40 %) and -II (yield 10 %) of siomycin A cis-butenedioic acid.

° Half ester -I of siomycin A with cis-butenedioic acid Powder. Rf value on thin-layer chromatography on silica gel GF (made by Merck company): Rf = 0 [Solvent: chloroform-methanol (8 : 2 by volume)]

Solubility: Well soluble in a mixture of chloroform and methanol, and in an aqueous solution of sodium hydrogencarbonate. Almost insoluble in ethyl ether, chloroform, and water.

Infrared absorption spectrum: $\gamma_{max}^{Nujol}$ cm$^{-1}$: 3400, 1725, 1645

Elementary analysis: Anhydrous compound; C, 49.77 %; H, 5.09 %; N, 14.42 %; S, 8.04 %, Hydrate of the compound; C, 47.91 %; H, 5.39 %; N, 13.01 %; S, 8.29 %; $H_2O$, 5.60 %.

EXAMPLE 10

To a solution of siomycin A (10.0 g) in pyridine (6 ml) is added cis-2-methylbutenedioic acid anhydride (0.78 g) and the mixture is treated as described in Example 1 to give the half esters -I (yield 40 %) and -II (yield 15 %) of siomycin A with cis-2-methylbutenedioic acid.

° Half ester -I of siomycin A with cis-2-methylbutenedioic acid Powder. Rf value on thin-layer chromatography on silica gel GF (made by Merck company): Rf = 0 [solvent: chloroform-methanol (8 : 2 by volume)]

Solubility: Well soluble in a mixture of chloroform and methanol, and in an aqueous solution of sodium hydrogencarbonate. Almost insoluble in ethyl ether, chloroform and water.

Infrared absorption spectrum: $\gamma_{max}^{Nujol}$ cm$^{-1}$ : 1730, 1660–1670

Elementary analysis: Anhydrous compound; C, 50.23 %; H, 5.16 %; N, 14.31 %; S, 8.35 %, Hydrate of the compound; C, 49.24 %; H, 5.19 %; N, 13.59 %; S, 8.06 %; $H_2O$, 7.03 %.

° Half ester -II of siomycin A with cis-2-methylbutenedioic acid Powder. Melting point: The compound turns brown at about 200°C and decomposes at over 260°C. Rf value on thin-layer chromatography on silica gel GF (made by Merck company): Rf = 0.37 [Solvent: chloroform-methanol (8 : 2 by volume)]

Solubility: Well soluble in a mixture of chloroform and methanol, and in an aqueous solution of sodium hydrogencarbonate. Almost insoluble in ethyl ether, chloroform and water.

Infrared absorption spectrum: $\gamma_{max}^{Nujol}$ cm$^{-1}$: 1730, 1650–1670

Elementary analysis: Anhydrous compound; C, 51.38 %; H, 5.26 %; N, 14.79 %; S, 8.87 %, Hydrate of the compound; C, 49.43 %; H, 5.48 %; N, 13.80 %; S, 8.55 %; $H_2O$, 5.45 %.

EXAMPLE 11

To a solution of siomycin A (300 mg) in pyridine (1.8 ml) is added cyclohexane-1,2-dicarboxylic acid anhydride (180 mg). The mixture is treated according to the manner described in Example 1 to give the half esters -I (yield 40 %) and -II (yield 40 %) of siomycin A with cyclohexane-1,2-dicarboxylic acid.

° Half ester -I of siomycin A with cyclohexane-1,2-dicarboxylic acid Powder. Rf value on thin-layer chromatography on silica gel GF (made by Merck company): Rf = 0.20–0.44 [Solvent: chloroform-methanol (8 : 2 by volume)]

Solubility: Well soluble in a mixture of chloroform and methanol, and in an aqueous solution of sodium hydrogencarbonate. Almost insoluble in ethyl ether, chloroform and water.

Infrared absorption spectrum: $\gamma_{max}^{Nujol}$ cm$^{-1}$: 3400, 1735, 1650–1670

Elementary analysis: Anhydrous compound; C, 52.36 %; H, 5.60 %; N, 13.38 %; S, 8.31 %, Hydrate of the compound; C, 50.31 %; H, 5.54 %; N, 12.88 %; S, 8.04 %; $H_2O$, 4.36 %.

°Half ester -II of siomycin A with cyclohexane-1,2-dicarboxylic acid Powder. Rf value on thin-layer chromatography on silica gel GF (made by Merck company): Rf = 0.52 [Solvent: chloroform-methanol (8 : 2 by volume)]

Solubility: Well soluble in a mixture of chloroform and methanol, and in an aqueous solution of sodium hydrogencarbonate. Almost insoluble in ethyl ether, chloroform and water.

Infrared absorption spectrum: $\gamma_{max}^{Nujol}$ cm$^{-1}$ : 3360–3400, 1730, 1650–1670

Elementary analysis: Anhydrous compound; C, 52.74 %; H, 5.76 %; N, 13.95 %; S, 8.68 %, Hydrate of the compound; C, 50.69 %; H, 5.58 %; N, 13.52 %; S, 8.39 %; $H_2O$, 4.86 %.

EXAMPLE 12

To a solution of siomycin A (0.5 g) in pyridine (3 ml) is added 1,2-benzenedicarboxylic acid anhydride (0.3 g) and the mixture is treated according to the manner described in Example 1 to give the half esters -I (yield 45 %), -II (yield 15 %) and -III (yield 15 %) of siomycin A with 1,2-benzenedicarboxylic acid.

° Half ester -I of siomycin A with 1,2-benzenedicarboxylic acid. Powder. Rf value on thin-layer chromatography on silica gel GF (made by Merck company) : Rf = 0–0.1 [Solvent: chloroform-methanol (8 : 2 by volume)]

Infrared absorption spectrum: $\gamma_{max}^{Nujol}$ cm$^{-1}$ : 1730 (shoulder), 1720 (shoulder), 1670

Elementary analysis: Anhydrous compound; C, 52.49 %; H, 5.30 %; N, 13.98 %; S, 8.33 %; Hydrate of the compound; C, 50.76 %; H, 5.48 %; N, 13.18 %; S, 8.13 %; $H_2O$, 5.07 %.

° Half ester -II of siomycin A with 1,2-benzenedicarboxylic acid Powder. Rf value on thin-layer chromatography on silica gel GF (made by Merck company) : Rf = 0.21 [Solvent: chloroform-methanol (8 : 2 by volume)]

Infrared absorption spectrum: $\gamma_{max}^{Nujol}$ cm$^{-1}$ : 1730, 1720, 1670

Elementary analysis: Anhydrous compound, C, 53.15 %; H, 5.58 %; N, 14.09 %; S, 8.76 %, Hydrate of the compound; C, 51.02 %; H, 5.37 %; N, 13.51 %; S, 8.38 %; $H_2O$, 4.25 %.

° Half ester -III of siomycin A with 1,2-benzenedicarboxylic acid Powder. Rf value on thin-layer chromatography on silica gel GF (made by Merck company): Rf = 0.40 [Solvent: chloroform-methanol (8 : 2 by volume)]

Infrared absorption spectrum: $\gamma_{max}^{Nujol}$ cm$^{-1}$ 1730, 1640–1670

Elementary analysis: Anhydrous compound; C, 52.23 %; H, 5.26 %; N, 14.38 %; S, 8.75 %; Hydrate of the compound; C, 50.98 %; H, 5.41 %; N, 13.35 %; S, 8.37 %; H$_2$O, 5.73 %.

What we claim is:

1. Half ester -I of siomycin A with butanedioic acid, yellowish powder, melting at 265° to 280°C with decomposition, containing the elements carbon, hydrogen, oxygen, nitrogen and sulfur in substantially the following proportions by weight: in the form of anhydrous compound; C, 50.42 %; H, 5.10 %; N, 14.57 %; S, 7.93 %, in the form of hydrate of the compound; C, 45.77 %; H, 5.45 %; N, 12.21 %; S, 7.62 %; H$_2$O, 10.68 %, having Rf of zero on thin-layer chromatography on silica gel GF (made by Merck company) [chloroform-methanol (8 : 2 by volume) solvent] having a specific rotation of $[\alpha]_D^{25}$ −63.2±2.0° (c = 0.525, in methanol), having a neutralization equivalent of 500, and showing an infrared absorption spectrum defined in FIG. 1 and an ultraviolet absorption spectrum defined in FIG. 2, and pharmaceutically acceptable salts thereof.

2. Half ester -II of siomycin A with butanedioic acid, colorless or pale yellowish powder, showing no definite decomposition point, turning yellow at around 200°C, then changing progressively to brown, then deep brown, containing the elements carbon, hydrogen, oxygen, nitrogen and sulfur in substantially the following proportions by weight: in the form of anhydrous compound; C, 48.52 %; H, 5.04 %; N, 14.76 %; S, 8.02 % in the form of hydrate of the compound; C, 45.69 %; H, 5.35 %; N, 13.32 %; S, 7.89 %; H$_2$O, 8.80 %, having Rf of 0.3 on thin-layer chromatography on silica gel GF (made by Merck company) [chloroform-methanol (8 : 2 by volume) solvent], having a specific optical rotation of $[\alpha]_D^{25}$ −144.0±3.7° (c = 0.507 in methanol), having a neutralization equivalent of 780, and showing an infrared absorption spectrum defined in FIG. 3 and an ultraviolet absorption spectrum defined in FIG. 2, and pharmaceutically acceptable salts thereof.

3. Half ester -I of siomycin A with pentanedioic acid, yellowish powder, having no define melting point or definite decomposition point, changing progressively from yellow to brown at around 200°C, containing the elements carbon, hydrogen, oxygen, nitrogen and sulfur in substantially the following proportions by weight: in the form of anhydrous compound; C, 49.61 %; H, 5.14 %; N, 14.37 %; S, 8.53 %, in the form of hydrate of the compound; C, 46.35 %; H, 5.70 %; N, 11.51 %; S, 7.75 %; H$_2$O, 10.45 %, having Rf of zero on thin-layer chromatography on silica gel GF (made by Merck company) [chloroform-methanol (8 : 2 by volume) solvent], having a specific optical rotation of $[\alpha]_D^{22.5}$ −68.7±2.2° (c = 0.504 in methanol), and showing an infrared absorption spectrum defined in FIG. 4 and an ultraviolet absorption spectrum defined in FIG. 5, and pharmaceutically acceptable salts thereof.

4. Half ester -II of siomycin A with pentanedioic acid, pale yellowish powder, having no definite melting or decomposition point, turning yellow at around 200°C, then changing progressively to brown, containing the elements carbon, hydrogen, oxygen, nitrogen and sulfur in substantially the following proportions by weight: in the form of anhydrous compound; C, 51.59 %; H, 5.18 %; N, 15.03 %; S, 9.30 %; in the form of hydrate of the compound; C, 49.06 %, H, 5.04 %; N, 12.85 %; S, 8.48 %; H$_2$O, 7.13 %, having Rf of 0.49 on thin-layer chromatography on silica gel GF (made by Merck company) [chloroform-methanol (8 : 2 by volume) solvent], having a specific optical rotation of $[\alpha]_D^{22.5}$ −84.0±4.1° (c = 0.306 in methanol), and showing an infrared absorption spectrum defined in FIG. 6 and an ultraviolet absorption spectrum defined in FIG. 5, and pharmaceutically acceptable salts thereof.

5. Half ester -I of siomycin A with hexanedioic acid, pale yellowish powder, showing no definite melting point or decomposition point, turning yellow at around 200°C, then changing progressively to brown, containing the elements carbon, hydrogen, oxygen, nitrogen and sulfur in substantially the following proportions by weight: in the form of anhydrous compound; C, 51.42 %; H, 5.36 %; N, 13.32 %; S, 8.26 %, in the form of hydrate of the compound; C, 49.25 %; H, 5.39 %; N, 12.29 %; S, 7.81 %; H$_2$O, 5.44 %, having Rf of 0.10 on thin-layer chromatography on silica gel GF (made by Merck company)[chloroform-methanol (8 : 2 by volume)solvent], having a specific optical rotation of $[\alpha]_D^{23}$ −61.5±3.3° (c = 0.314 in a mixture of chloroform and methanol (1 : 1 by volume), and showing an infrared absorption spectrum defined in FIG. 7 and an ultraviolet absorption spectrum defined in FIG. 8, and pharmaceutically acceptable salts thereof.

6. Half ester -II of siomycin A with hexanedioic acid, colorless crystalline powder, showing no definite melting point or decomposition point, turning yellow at around 200°C, then changing progressively to brown, containing the elements carbon, hydrogen, oxygen, nitrogen and sulfur in substantially the following proportions by weight: in the form of anhydrous compound; C, 51.18 %; H, 5.24 %; N, 14.73 %; S, 8.86 % in the form of hydrate of the compound; C, 48.74 %; H, 5.56 %; N, 13.57 %; S, 8.65 %; H$_2$O, 3.83 %, having Rf of 0.56 on thin-layer chromatography on silica gel GF (made by Merck company)[chloroform-methanol(8 : 2 by volume)solvent], having a specific optical rotation of $[\alpha]_D^{23.5}$ −118.4±5.3° (c = 0.304 in a mixture of chloroform and methanol (1 : 1 by volume), and showing an infrared absorption spectrum defined in FIG. 9 and an ultraviolet absorption spectrum defined in FIG. 8, and pharmaceutically acceptable salts thereof.

7. Half ester -III of siomycin A with hexanedioic acid, pale yellowish powder, showing no definite melting point or decomposition point, turning yellow at around 200°C, then changing progressively to brown, containing the elements carbon, hydrogen, oxygen, nitrogen and sulfur in substantially the following proportions by weight: in the form of anhydrous compound; C, 51.89 %; H, 5.77 %; N, 14.56 %; S, 8.97 % in the form of hydrate of the compound; C, 49.37 %; H, 5.53 %; N, 13.78 %; S, 8.46 %; H$_2$O, 5.44 %, having Rf of 0.48 on thin-layer chromatography on silica gel GF (made by Merck company)[chloroform-methanol(8 : 2 by volume)solvent], having a specific optical rotation of $[\alpha]_D^{23.5}$ −140.2±6.0° (c = 0.301, in a mixture of chloroform and methanol (1 : 1 by volume), and showing an infrared absorption spectrum defined in FIG. 10 and an ultraviolet absorption spectrum defined in FIG. 8, and pharmaceutically acceptable salts thereof.

8. Half ester -I of siomycin A with heptanedioic acid, pale yellowish powder, showing no definite melting point or decomposition point, turning yellow at around 200°C, then changing progressively to brown, containing the elements carbon, hydrogen, oxygen, nitrogen and sulfur in substantilly the following proportions by weight: in the form of anhydrous compound; C, 52.41

%; H, 5.62 %; N, 13.41 %; S, 8.26 %, in the form of hydrate of the compound; C, 50.21 %; H, 5.60 %; N, 12.54 %; S, 7.91 %; H$_2$O, 3.56 %, having Rf of 0.1 on thin-layer chromatography on silica gel GF (made by Merck company)[chloroform-methanol (8 : 2 by volume)solvent], having a specific optical rotation of $[\alpha]_D^{23.5}$ −73.2±3.5° (c = 0.325, in a mixture of chloroform and methanol (1 : 1 by volume), and showing an infrared absorption spectrum defined in FIG. 13 and an ultraviolet absorption spectrum defined in FIG. 14, and pharmaceutically acceptable salts thereof.

9. Half ester -II of siomycin A with heptanedioic acid, pale yellowish powder, showing no definite melting point or decomposition point, turning yellow at around 200°C, then changing progressively to brown, containing the elements carbon, hydrogen, oxygen, nitrogen and sulfur in substantially the following proportions by weight: in the form of anhydrous compound; C, 53.21 %; H, 5.72 %; N, 14.07 %; S, 8.73 %, in the form of hydrate of the compound; C, 50.68 %, H, 5.63 %; N, 13.48 %; S, 8.36 %; H$_2$O, 4.94 %, having Rf of 0.47 on thin-layer chromatography on silica gel GF (made by Merck company) [chloroform-methanol (8 : 2 by volume)solvent], having a specific optical rotation of $[\alpha]_D^{23.5}$ −128.6±5.5° (c = 0.308, in a mixture of chloroform and methanol (1 : 1 by volume), and showing an infrared absorption spectrum defined in FIG. 15 and an ultraviolet absorption spectrum defined in FIG. 14, and pharmaceutically acceptable salts thereof.

10. Half ester -III of siomycin A with heptanedioic acid, almost colorless crystalline powder, showing no definite melting point or decomposition point, turning yellow at around 200°C, then changing progressively to brown, containing the elements carbon, hydrogen, oxygen, nitrogen and sulfur in substantially the following proportions by weight: in the form of anhydrous compound; C, 52.00 %; H, 5.34 %; N, 14.33 %; S, 8.73 %, in the form of hydrate of the compound; C, 48.74 %; H, 5.49 %; N, 13.36 %; S, 8.38 %; H$_2$O, 6.40, having Rf of 0.56 on thin-layer chromatography on silica gel GF (made by Merck company) [chloroform-methanol (8 : 2 by volume)solvent], having a specific optical rotation of $[\alpha]_D^{23.5}$ −119.3±5.0° (c = 0.322, in a mixture of chloroform and methanol (1 : 1 by volume), and showing an infrared absorption spectrum defined in FIG. 16 and an ultraviolet absorption spectrum defined in FIG. 14, and pharmaceutically acceptable salts thereof.

* * * * *